US011964009B2

(12) United States Patent
Kawaoka et al.

(10) Patent No.: US 11,964,009 B2
(45) Date of Patent: Apr. 23, 2024

(54) CELLS FOR PRODUCING INFLUENZA VIRUS AND METHOD FOR PRODUCING INFLUENZA VIRUS (71) Applicant: Japan Science and Technology Agency, Kawaguchi (JP)

(72) Inventors: Yoshihiro Kawaoka, Minato-ku (JP); Tokiko Watanabe, Suginami-ku (JP); Eiryo Kawakami, Yokohama (JP); Shinji Watanabe, Suginami-ku (JP)

(73) Assignee: Japan Science and Technology Agency, Kawaguchi (JP)

( * ) Notice: Subject to any disclaimer, the term of this patent is extended or adjusted under 35 U.S.C. 154(b) by 257 days.

(21) Appl. No.: 16/453,464

(22) Filed: Jun. 26, 2019

(65) Prior Publication Data

US 2019/0314489 A1 Oct. 17, 2019

Related U.S. Application Data (62) Division of application No. 15/511,988, filed as application No. PCT/JP2015/076681 on Sep. 18, 2015, now Pat. No. 10,369,210.

(30) Foreign Application Priority Data

Sep. 22, 2014 (JP) ................. 2014-192753

(51) Int. Cl.
| C12N 5/00 | (2006.01) |
| A61K 39/145 | (2006.01) |
| C12N 5/071 | (2010.01) |
| C12N 5/10 | (2006.01) |
| C12N 7/02 | (2006.01) |
| C12N 7/08 | (2006.01) |
| C12N 15/113 | (2010.01) |

(52) U.S. Cl.
CPC .............. *A61K 39/145* (2013.01); *C12N 5/00* (2013.01); *C12N 5/0686* (2013.01); *C12N 5/10* (2013.01); *C12N 7/02* (2013.01); *C12N 7/08* (2013.01); *C12N 15/113* (2013.01); *C12N 2760/16051* (2013.01)

(58) Field of Classification Search
CPC ....... C12N 5/0686; C12N 5/10; C12N 15/113
See application file for complete search history.

(56) References Cited

U.S. PATENT DOCUMENTS

| 2005/0262577 | A1 | 11/2005 | Guelly |
| 2007/0287666 | A1 | 12/2007 | Fraser et al. |
| 2011/0008350 | A1 | 1/2011 | De Strooper et al. |
| 2012/0077806 | A1* | 3/2012 | Donato ............ C07D 213/68 |
| | | | 514/227.8 |

FOREIGN PATENT DOCUMENTS

| CN | 102018965 A | 4/2011 | |
| WO | WO 2010/134939 A2 | 11/2010 | |
| WO | WO-2010134939 A2 * | 11/2010 | ........... A61K 31/407 |
| WO | WO 2011/005765 A1 | 1/2011 | |
| WO | WO 2011/072247 A2 | 6/2011 | |
| WO | WO 2013/106548 A1 | 7/2013 | |
| WO | WO-2013106548 A1 * | 7/2013 | ........... A61K 39/145 |
| WO | 2014/123967 A2 | 8/2014 | |

OTHER PUBLICATIONS

Mayer et al , Identification of Cellular Interaction Partners of the Influenza Virus Ribonucleoprotein Complex and Polymerase Complex Using Proteomic-Based Approaches, Journal of Proteome Research, 2007, 6: 672-682 (Year: 2007).*
Spurgers et al, Identification of Essential Filovirion-associated Host Factors by Serial Proteomic Analysis and RNAi Screen, Molecular & Cellular Proteomics, 2010, vol. 9, issue 12: 2690-2703 (Year: 2010).*
Zhao et al, Proteomic analysis of the lungs of mice infected with different pathotypes of H5N1 avian influenza viruses, Proteomics, 2012, 12: 1970-1982 (Year: 2012).*
Iwai et al , Relevance of signaling molecules for apoptosis induction on influenza A virus replication, Biochemical and Biophysical Research Communications, 2013, 441: 531-537 (Year: 2013).*
Kroeker et al , Influenza A Infection of Primary Human Airway Epithelial Cells Up-Regulates Proteins Related to Purine Metabolism and Ubiquitin-Related Signaling, Journal of Proteome Research, Jun. 2013, 12: 3139-3151 (Year: 2013).*
LeBouder et al , Annexin II Incorporated into Influenza Virus Particles Supports Virus Replication by Converting Plasminogen into Plasmin, Journal of Virology, Jul. 2008, vol. 82, No. 14: 6820-6828 (Year: 2008).*
Noriko Kishida, et al., "Evaluation of Influenza Virus A/H3N2 and B Vaccines on the Basis of Cross-Reactivity of Postvaccination Human Serum Antibodies against Influenza Viruses A/H3N2 and B Isolated in MDCK Cells and Embryonated Hen Eaggs", Clinical and Vaccine Immunology, vol. 19, No. 6. pp. 897-908, (Jun. 2012).

(Continued)

*Primary Examiner* — Ekaterina Poliakova-Georgantas
(74) *Attorney, Agent, or Firm* — Oblon, McClelland, Maier & Neustadt, L.L.P.

(57) ABSTRACT

The present invention provides cells which have a high ability to propagate influenza virus, are suitable for use in production of an influenza virus for preparing a vaccine, and are able to be cultured in vitro, and a method for producing an influenza virus using the cells. That is, the present invention provides cells for producing an influenza virus in which expression of one or more genes that encode proteins involved in an effect of suppressing influenza virus production in a cell is suppressed and the gene is at least one selected from the group including ACTG1 gene and the like, and a method for producing an influenza virus that includes infecting the cells for producing an influenza virus with an influenza virus and then culturing.

4 Claims, 1 Drawing Sheet

Specification includes a Sequence Listing.

(56) References Cited

OTHER PUBLICATIONS

Gabriele Neumann, et al., "Generation of influenza A viruses entirely from cloned cDNAs", Proc. Natl. Acad. Sci. USA, vol. 96, pp. 9345-9350, (Aug. 1999).
K. Toblta, et al., "Plaque Assay and Primary Isolation of Influenza A Viruses in an Established Line of Canine Kidney Cells (MDCK) in the Presence of Trypsin", Med. Microbiol. Immunol., vol. 162, pp. 9-14, (1975).
Hiroichi Ozaki et al., "Generation of High-Yielding Influenza A Viruses in African Green Monkey Kidney (Vero) Cells by Reverse Genetics", Journal of Virology, vol. 78, No. 4, pp. 1851-1857, (Feb. 2004).
Alexander Karlas, et al., "Genome-wide RNAE screen identifies human host factors crucial for influenza virus replication", Nature, vol. 463, Total 7 Pages, (Feb. 11, 2010).
International Search Report dated Dec. 15, 2015 in PCT/JP2015/076681 Filed Sep. 18, 2015.
Partial Supplementary European Search Report dated Jan. 15, 2018 in Patent Application No. 15844041.2.
Satoshi Kakugawa, et al., "RuvB-Like Protein 2 Is a Suppressor of Influenza A Virus Polymerases", Journal of Virology, vol. 83, No. 13, XP055056260, Jul. 2009. pp. 6429-6434 and cover page.
Tomohiro Torii, et al., "Arf6 guanine-nucleotide exchange factor, cytohesin-2, interacts with actinin-1 to regulate neurite extension", Cellular Signaling, vol. 24, No. 9, XP028496211, May 2012, pp. 1872-1882.
Extended European Search Report dated Jun. 26, 2020 in corresponding European Patent Application No. 20167102.1, 7 pages.
Weibo Luo et al: "p24A, a Type I Transmembrane Protein, Controls ARF1-dependent Resensitization of Protease-activated Receptor-2 by Influence on Receptor Trafficking", Journal of Biological Chemistry, vol. 282, No. 41, XP55705876, Oct. 12, 2007, pp. 30246-30255 and cover page.
Office Action dated Aug. 17, 2021, in Japan Patent Application No. 2020-114286 (with English-language Translation).

\* cited by examiner

CELLS FOR PRODUCING INFLUENZA VIRUS AND METHOD FOR PRODUCING INFLUENZA VIRUS

CROSS REFERENCE TO RELATED APPLICATIONS

The present application is a divisional of U.S. patent application Ser. No. 15/511,988, filed on Mar. 16, 2017, which is a 35 U.S.C. § 371 national stage patent application of international patent application PCT/JP2015/076681, filed on Sep. 18, 2015, which claims priority to Japanese patent application JP 2014-192753, filed on Sep. 22, 2014.

TECHNICAL FIELD

The present invention relates to cells which have a high ability to propagate influenza virus are suitable for use in production of an influenza virus for preparing a vaccine, and are able to be cultured in vitro, and a method for producing an influenza virus using the cells.

Priority is claimed on Japanese Patent Application No. 2014-192753, filed Sep. 22, 2014, the content of which is incorporated herein by reference.

BACKGROUND ART

Influenza viruses cause epidemic diseases every year and sometimes cause pandemic diseases taking millions of victims. Influenza infection is generally prevented by preventive inoculation with a vaccine. The vaccine is obtained by inactivating influenza virus particles or partially decomposed products thereof. According to preventive inoculation with influenza vaccines, it is possible to reduce the risk of serious complications such as pneumonia, hospitalization and death when a person is infected with influenza.

Currently, vaccines are produced by inoculating embryonated chicken eggs with influenza viruses. Therefore, a large amount of embryonated chicken eggs need to be prepared for vaccine production. In addition, since production takes about six months, mass production of unexpected vaccines is difficult. In addition, allergic reactions due to egg components need to be considered.

Further, when influenza viruses are grown in chicken eggs, mutations are introduced into the viruses' genes, and antigenicity of the viruses changes in many cases. Actually, in recent years, in H3N2 type and B-type vaccines, antigenicity of a selected vaccine strain has matched that of an epidemic strain. However, mutations have been introduced into vaccine virus genes at the production stage, and antigenicity of produced vaccines has changed from the original vaccine strains. Therefore, there are situations in which "the vaccine effect is low even when an epidemic strain has been predicted correctly" (refer to Non Patent Literature 1).

CITATION LIST

Non Patent Literature

[Non Patent Literature 1]
Kishida et al., Clinical and Vaccine Immunology, 2013, vol. 19, p. 897 to 908.
[Non Patent Literature 2]
Neumann, et al., Proceedings of the National Academy of Sciences of the United States of America, 1999, vol. 96, p. 9345 to 9350.
[Non Patent Literature 3]
Tobita, et al., Medical microbiology and immunology, 1975, vol. 162, p. 9 to 14.

SUMMARY OF INVENTION

Technical Problem

Cultured cells are used for vaccine production as an alternative to chicken eggs. This vaccine production has already been approved in Europe and the United States and there is demand for approval in Japan. However, since cultured cells is worse in an ability of cultured cells to propagate influenza virus than chicken eggs, the development of a system for efficiently propagating influenza virus in cultured cells is the most important task.

The present invention provides cells which have a high ability to propagate influenza virus, are suitable for use in production of an influenza virus for preparing a vaccine, and are able to be cultured, and a method for producing an influenza virus using the cell.

Solution to Problem

The inventors have conducted extensive studies, identified 1292 human proteins that interact with influenza virus proteins according to an immunoprecipitation method using a cell lysate of HEK293 cells derived from a human embryonic kidney, and then identified proteins in which influenza virus propagation was significantly improved without excessively impairing a proliferative ability of cells when an expression level was suppressed among these human proteins using RNA interference, and thus completed the present invention.

That is, cells for producing an influenza virus and a method for producing an influenza virus according to the present invention are the following [1] to [9].

[1] Cells for producing an influenza virus which are cells in which expression of one or more genes in the chromosomes is suppressed and which are able to be cultured in vitro, wherein the gene is at least one gene selected from the group including ACTG1 gene, ACTN1 gene, ATCAY gene, CCT6A gene, COPS7B gene, DAP3 gene, ERLIN2 gene, GNAI2 gene, GTF3C5 gene, HNRPAB gene, KHSRP gene, KRT18 gene, MTCH1 gene, PPP2R1A gene, PRPS1 gene, RAB18 gene, RAB3A gene, RAP1B gene, RPS19 gene, RPS7 gene, S100A10 gene, SFRS7 gene, SLC2A12 gene, TMED2 gene, and USP10 gene.

[2] The cells for producing an influenza virus according to [1], wherein the gene is deleted or disrupted.

[3] The cells for producing an influenza virus according to [1] or [2], wherein the gene is at least one selected from the group including ACTG1 gene, ACTN1 gene, DAP3 gene, GNAI2 gene, GTF3C5 gene, KRT18 gene, MTCH1 gene, PRPS1 gene, RPS19 gene, S100A10 gene, SFRS7 gene, SLC2A12 gene, USP10 gene, PPP2R1A gene, and TMED2 gene.

[4] The cells for producing an influenza virus according to any of [1] to [3], wherein the cells for producing an influenza virus are mammal-derived cells.

[5] The cells for producing an influenza virus according to [4], wherein the cells for producing an influenza virus are human-derived cells.

[6] The cells for producing an influenza virus according to [4],
wherein the cells for producing an influenza virus are kidney-derived cells.
[7] The cells for producing an influenza virus according to any one of [1] to [6],
wherein the cells for producing an influenza virus are used to prepare an influenza virus vaccine.
[8] A method for producing an influenza virus including
infecting the cells for producing an influenza virus according to any one of [1] to [7] with an influenza virus and then culturing.
[9] The method for producing an influenza virus according to [8],
wherein the influenza virus is an influenza virus for preparing an influenza virus vaccine.

Advantageous Effects of Invention

In cells for producing an influenza virus according to the present invention, expression of a specific gene is suppressed and so an ability to propagate influenza virus of the cells is higher than that of cells in which expression of the gene and the like are not suppressed. Therefore, it is possible to efficiently propagate an influenza virus using the cells for producing an influenza virus, and particularly it is possible to efficiently produce an influenza virus for vaccine preparation.

DESCRIPTION OF EMBODIMENTS

Figure 1:
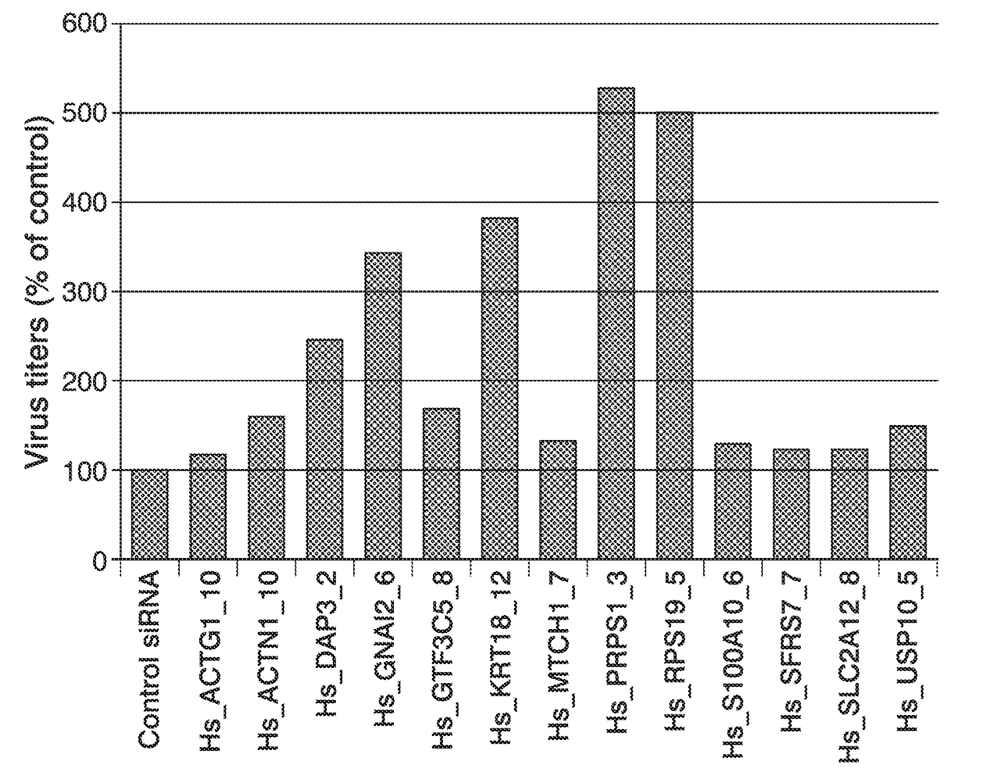
The FIGURE is a diagram showing results obtained by calculating virus titers (relative value (%) to a control) of Vero cells into which siRNAs are introduced in Example 2.

Cells for producing an influenza virus according to the present invention are cells (cultured cells) that can be cultured in vitro and cells in which expression of a gene (hereinafter referred to as a "FluV propagation suppressing gene" in some cases) exhibiting an influenza virus propagation promoting effect when expression is suppressed is suppressed. In the cells, expression of at least one type of FluV propagation suppressing gene in the chromosomes is suppressed. Therefore, it is possible to efficiently propagate an influenza virus using the cells.

Specific examples of the FluV propagation suppressing gene whose expression is suppressed in the cells for producing an influenza virus according to the present invention include ACTG1 gene, ACTN1 gene, ATCAY gene, CCT6A gene, COPS7B gene, DAP3 gene, ERLIN2 gene, GNAI2 gene, GTF3C5 gene, HNRPAB gene, KHSRP gene, KRT18 gene, MTCH1 gene, PPP2R1A gene, PRPS1 gene, RAB18 gene, RAB3A gene, RAP1B gene, RPS19 gene, RPS7 gene, S100A10 gene, SFRS7 gene, SLC2A12 gene, TMED2 gene, and USP10 gene. As will be described in the following examples, in cultured cells in which expression of these genes is suppressed, and particularly, in human-derived cultured cells, an ability to propagate an influenza virus is favorable and a proliferative ability of the cells themselves is not suppressed much compared to cells in which expression is not suppressed. That is, by suppressing expression of these genes in cells, an influenza virus propagation promoting effect is obtained without excessively impairing a proliferative ability of the cells themselves. In addition, since these genes encode proteins that directly or indirectly bind to any of 11 types of influenza virus proteins (PB2, PB1, PA, HA, NP, NA, M1, M2, NS1, NS2, and PB1-F2), this indicates that an interaction between proteins that these genes encode and influenza virus proteins plays an important role in suppressing influenza virus propagation.

In the cells for producing an influenza virus according to the present invention, expression of one type of FluV propagation suppressing genes may be suppressed and expression of two or more types of FluV propagation suppressing genes may be suppressed. As the cells for producing an influenza virus according to the present invention, cells in which expression of at least one selected from the group including ACTG1 gene, ACTN1 gene, DAP3 gene. GNAI2 gene, GTF3C5 gene, KRT18 gene, MTCH1 gene. PRPS1 gene, RPS19 gene. S100A10 gene, SFRS7 gene, SLC2A12 gene, USP10 gene, PPP2R1A gene, and TMED2 gene is suppressed are preferable. This is because an influenza virus propagation promoting effect according to suppression of expression of these FluV propagation suppressing genes is confirmed not only in human-derived cells but also in monkey-derived cells or canine-derived cells.

As the cells for producing an influenza virus according to the present invention, cells in which an expression level of the FluV propagation suppressing gene is reduced to 50% or less of an expression level of the genes in cells of the same type before expression suppression are preferable, cells in which an expression level of the FluV propagation suppressing gene is reduced to 75% or less of an expression level of the genes in cells of the same type before expression suppression are more preferable, and cells in which an expression level of the FluV propagation suppressing gene is reduced to 80% or less of an expression level of the genes in cells of the same type before expression suppression are most preferable. For example, when the cells for producing an influenza virus according to the present invention are cells in which expression of one type of FluV propagation suppressing genes of cultured cell line HEK293 cells is suppressed, as the cells for producing an influenza virus according to the present invention, cells in which expression of the FluV propagation suppressing gene is suppressed to an extent at which an expression level of the FluV propagation suppressing gene is reduced to 50% or less of an expression level of the FluV propagation suppressing gene in HEK293 cells are preferable.

In order to suppress expression of the FluV propagation suppressing gene in cultured cells, an amount of transcription (an expression level) of the FluV propagation suppressing gene may be reduced, the FluV propagation suppressing gene itself may be removed from chromosomes, and a mutation may be introduced into the FluV propagation suppressing gene and the gene may be disrupted. When the FluV propagation suppressing gene is removed from the chromosomes, the full length of the gene may be removed, a region involved in expression control such as a promoter portion may be partially removed, or a coding region of the gene may be partially removed so that a protein in a portion in which a function of the gene is deleted is expressed. Reduction of a gene transcription level, gene deletion, gene disruption and the like can be performed by a general method.

In the cells for producing an influenza virus according to the present invention, suppression of expression of the FluV propagation suppressing gene may be temporary or expression of the FluV propagation suppressing gene may be stably suppressed. In consideration of stability of an influenza virus propagation promoting effect, as the cells for producing an influenza virus according to the present invention, cells in which expression of the FluV propagation suppressing gene is stably suppressed are preferable.

Among the cells for producing an influenza virus according to the present invention, cells in which suppression of expression of the FluV propagation suppressing gene is temporary can be prepared using, for example, RNA interference. Specifically, a small interfering RNA (siRNA), a short hairpin RNA (shRNA) or a micro RNA (miRNA) having a double-stranded structure including a sense strand and an antisense strand of a partial region (RNA interference (RNAi) target region) of cDNA of the FluV propagation suppressing gene can be introduced into cultured cells for preparation. In addition, an RNAi inducible vector through which siRNA and the like can be produced in cultured cells may be introduced into cultured cells. siRNA, shRNA, miRNA, and an RNAi inducible vector can be designed and prepared from base sequence information of cDNA of a target FluV propagation suppressing gene using a general method. In addition, the RNAi inducible vector can be prepared by inserting a base sequence of an RNAi target region into a base sequence of commercially available various RNAi vectors. Further, siRNA, shRNA, miRNA, and an RNAi inducible vector can be introduced into cultured cells by, for example, an electroporation method, a lipofection method, and a calcium phosphate method.

Among the cells for producing an influenza virus according to the present invention, cells in which expression of the FluV propagation suppressing gene is stably suppressed can be prepared by, for example, a method of integrating siRNA, shRNA and the like into the chromosomes of cultured cells through a retroviral vector. A retroviral vector (a retroviral vector for siRNA expression) for integrating siRNA or shRNA into the chromosomes can be prepared by, for example, deleting structural genes gag, pol and env necessary for retrovirus replication and introducing a retroviral plasmid vector for integrating siRNA or shRNA into a packaging cell in which gag, pol and env are expressed. The retroviral vector for siRNA expression can be prepared using a commercially available kit such as Retrovirus Packaging Kit Eco/Ampho (code 6160/6161) (commercially available from Takara Bio Inc.). When the siRNA expression retroviral vector for expression of siRNA and the like of the FluV propagation suppressing gene is introduced into cultured cells, the cells for producing an influenza virus according to the present invention are obtained.

As the cells for producing an influenza virus according to the present invention, cells (FluV propagation suppressing gene deficient cells) in which the FluV propagation suppressing gene itself is deleted (removed) from the chromosomes and cells (FluV propagation suppressing gene-disrupted cells) in which the FluV propagation suppressing gene is disrupted by introducing a mutation according to base substitution, deletion, or insertion are particularly preferable. It is undeniable that siRNA and the like integrated into the chromosomes can disappear due to subculture. However, in cells in which the FluV propagation suppressing gene itself is deleted or mutated, there is no risk of restoring an expression level of the FluV propagation suppressing gene due to subculture. The FluV propagation suppressing gene deficient cells and FluV propagation suppressing gene-disrupted cells can be prepared by various methods that are generally used for removal of a specific gene from the chromosomes and gene mutagenesis.

For example, when an artificial nuclease (a chimeric protein in which a domain that specifically binds to DNA and a DNA cleavage domain of a restriction enzyme FokI are linked) is used, it is possible to prepare FluV propagation suppressing gene-disrupted cells. The artificial nuclease is bound to a specific region (a target sequence) in the chromosomes by the domain that specifically binds to DNA and then cuts chromosomal DNA when the DNA cleavage domain of the restriction enzyme FokI forms a dimer. Specifically, for example, in the target FluV propagation suppressing gene, a cleavage site is set in the gene region in the chromosomes, and two types of artificial nucleases having two adjacent partial base sequences sandwiching the cleavage site as target sequences are prepared and introduced into cultured cells. The artificial nuclease introduced into cultured cells binds to each adjacent target sequence in the chromosomes to form a dimer and cuts chromosomal DNA. A mutation (base deletion, insertion, or substitution) is introduced when the cut chromosomal DNA repairs nonhomologous end-joining or repairs homologous recombination. As a result, the FluV propagation suppressing gene is disrupted.

Examples of artificial nucleases include TAL effector nuclease (TALEN) using a Transcriptional Activator-Like (TAL) effector as a DNA binding domain and Zinc Finger Nuclease (ZFN) using Zinc-Finger as a DNA binding domain. The artificial nucleases can be prepared by a general method on the basis of base sequence information of the target FluV propagation suppressing gene. In addition, a commercially available kit, for example, GeneArt (registered trademark) Precision TALs (commercially available from Life Technologies Corporation), can be used for preparation.

In addition, FluV propagation suppressing gene-disrupted cells can be prepared using an RNA guided endonuclease (RGEN). RGEN is an RNA induced artificial nuclease derived from the CRISPR/Cas system, which is an acquired immune system of bacteria, and includes a guide RNA that recognizes a target sequence to be cut in the chromosomes and Cas9 endonuclease. Specifically, first, a guide RNA is designed on the basis of base sequence information of a target FluV propagation suppressing gene. Next, both an expression vector for expressing a guide RNA in a cell and an expression vector for expressing Cas9 endonuclease in a cell are introduced into cultured cells. The guide RNA expressed in the cell binds to a target sequence in the chromosome and Cas9 endonuclease that is expressed in the cell in the same manner recognizes the bound guide RNA and cut for each chromosomal DNA. A mutation (base deletion, insertion, or substitution) is introduced when the cut chromosomal DNA repairs nonhomologous end-joining or repairs homologous recombination. As a result, the FluV propagation suppressing gene is disrupted.

An expression vector for expressing an artificial nuclease and a guide RNA in a cell, an expression vector for expressing Cas9 endonuclease in a cell and the like can be introduced into cultured cells by, for example, an electroporation method, a lipofection method, and a calcium phosphate method.

When the cells for producing an influenza virus according to the present invention are prepared, cultured cells in which expression of the FluV propagation suppressing gene is suppressed are not particularly limited as long as an influenza virus can be infected into cells and can propagate in the cultured cells. In consideration of a type, a host and the like of an influenza virus to be produced, the cultured cells can be appropriately determined from among various cultured cells. For example, cultured cells derived from mammals such as humans, monkeys, mice, rats, hamsters, rabbits, pigs, horses, dogs, cats, and tigers; or birds such as chickens, ducks, quails, geese, ducks, turkeys, budgerigars, parrots, mandarin ducks, and swans can be used. In addition, tissues from which cultured cells are derived are not particularly limited. Cultured cells derived from, for example, a kidney, a lung, a liver, skin, connective tissues, an ovary, a uterus, blood cells, lymphatic tissues, a mouth, an esophagus, a stomach, a small intestine, a large intestine, and a fetus can be used. Specifically, among generally used cultured cells, HEK293 cells, MDCK (Madin-Darby canine kidney) cells, Vero cells, A549 cells, Calu-3 cells, HepG2 cells, NIH3T3 cells, 3T3-L1 cells, CHO cells, DF-1 cells, HeLa cells, HL-60 cells, Jurkat cells, Caco-2 cell and the like may be exemplified. Among these, HEK293 cells, MDCK cells, and Vero cells are more preferable because they have a favorable cell proliferative ability and are relatively easy to handle.

Also, human-derived cultured cells refer to cells obtained by artificially culturing cells collected from a human in vitro or cells sub-cultured from the cells. Similarly, kidney-derived cells refer to cells obtained by artificially culturing cells collected from a kidney of an animal in vitro or cells sub-cultured from the cells. These are similarly applied to cultured cells derived from other animal species or other tissues.

The cells for producing an influenza virus according to the present invention can be cultured under the same conditions as cultured cells before expression of the FluV propagation suppressing gene is suppressed. For example, mammal-derived cultured cells can be cultured under a 5% carbon dioxide atmosphere at 37° C. Examples of media used for culture include a Dulbecco's Modified Eagle's Medium (DMEM medium), an Eagle's minimum essential medium (EMEM medium), a minimum essential medium (MEM) a medium, and an RPMI-1640 medium. Various additives such as a serum, antibiotics, amino acids such as L-glutamine, sodium pyruvate, vitamins, insulin, transfer, selenium, and bicarbonate sodium salt can be contained in such media as necessary.

When an influenza virus is infected into the cells for producing an influenza virus according to the present invention and then cultured, the influenza virus propagates in the cells. The propagated influenza virus is secreted in the medium. Therefore, an influenza virus can be produced through an infection process in which an influenza virus is infected into cells for producing an influenza virus according to the present invention, a culture process in which the cells infected with an influenza virus are cultured in a culture medium and a virus collecting process in which a culture supernatant including the influenza virus is collected after the culture process. The influenza virus in the culture supernatant can be purified by a general method.

The influenza virus to be infected into the cells for producing an influenza virus according to the present invention may have any type. An A-type influenza virus or a B-type influenza virus is preferable. An influenza virus capable of infecting a mammal or a bird is more preferable. An influenza virus capable of infecting a human is most preferable.

Since cells for producing an influenza virus according to the present invention has a sufficient proliferative ability and a favorable ability to propagate influenza virus, it is possible to efficiently propagate the influenza virus through the cells. In addition, the cells has a lower risk of mutation in an influenza virus in the propagation process than a chicken egg. Therefore, the cells for producing an influenza virus according to the present invention are suitably used for producing an influenza virus for preparing a vaccine. Specifically, the virus infected into the cells for producing an influenza virus according to the present invention is an influenza virus for preparing an influenza virus vaccine.

EXAMPLES

Next, the present invention will be described in further detail with reference to examples, but the present invention is not limited to the following examples.

<Cell Culture>

In the following examples, HEK293 cells and Vero cells were cultured in a DMEM medium (commercially available from Sigma Aldrich) containing 10% fetal calf serum (FCS) and antibiotics under a 5% carbon dioxide atmosphere at 37° C. MDCK cells were cultured in a 5% newborn calf serum (NCS)-containing EMEM medium (commercially available from GIBCO) under a 5% carbon dioxide atmosphere at 37° C.

<Influenza Viruses>

Influenza viruses used in the following examples were A type influenza viruses (A/WSN/33, H1N1 subtype; WSN) unless otherwise described. The viruses were human-derived influenza viruses adapted to mice, prepared by a method (refer to Non Patent Literature 2) using reverse genetics, and propagated in MDCK cells. In addition, virus titers were measured by a plaque assay using MDCK cells (refer to Non Patent Literature 3).

Example 1

<Identification of Host Proteins that Interact with Influenza Virus Proteins>

First, the inventors identified host proteins that interact with influenza virus proteins using an immunoprecipitation method.

Specifically, first, a plasmid encoding a Flag fusion protein in which Flag tag was fused to the N-terminus or the C-terminus for 11 types of influenza virus proteins (PB2, PB1, PA, HA, NP, NA, M1, M2, NS1, NS2, and PB1-F2) was transfected into HEK293 cells, respectively. Transfection was performed using a TransIT 293 reagent (commercially available from Mirus Bio Corp). Cells cultured for 24 hours after the transfection were mixed in a cell lysis buffer (50 mM Tris-HCl (pH 7.5), 150 mM NaCl, 1 mM EDTA, 0.5% Nonidet P-40, protease inhibitor mixture Complete Mini (Roche, Mannheim, Germany)), incubated at 4° C. for 1 hour, and lysed to obtain a lysate. A supernatant collected by centrifuging the obtained lysate was added to an affinity gel (anti-FLAG M2 Affinity Gel commercially available from Sigma Aldrich) to which anti-Flag antibodies were bound and incubated at 4° C. for 18 hours. Then, the affinity gel was washed three times with a cell lysis buffer, then washed twice with an immunoprecipitation (IP) buffer (50 mM Tris-HCl (pH 7.5), 150 mM NaCl, 1 mM EDTA), and stirred with an IP buffer containing 0.5 mg/mL of FLAG peptides (F1804, commercially available from Sigma Aldrich) at 4° C. for 2 hours. Then, the affinity gel was removed through centrifugation and a supernatant was collected.

The collected supernatant was filtrated through an Ultrafree-MC filter (commercially available from Merck Millipore Corporation), and then the contained protein was identified through nano LC-MS/MS (nanoflow liquid chromatography tandem mass spectrometry) analysis. Q-STAR Elite (commercially available from AB SCIEX) coupled with Dina (commercially available from KYA technologies corporation) was used to analyze the mass spectrometry data. Co-immunoprecipitated proteins of HEK293 cells (host cells) were identified by comparing the obtained MS/MS signal with RefSeq (human protein database of National Center for Biotechnology Information). For this comparison, Mascot algorithm (version 2.2.04; commercially available from Matrix Science) was used under the following conditions: variable modifications, oxidation (Met), N-acetylation; maximum missed cleavages, 2; peptide mass tolerance, 200 ppm; MS/MS tolerance, 0.5 Da.). Protein identification required at least one MS/MS signal with a Mascot score that exceeded significantly greater the threshold value.

As a result, 388 host proteins were co-immunoprecipitated with PB2 proteins, 322 host proteins were co-immunoprecipitated with PB1 proteins, 304 host proteins were co-immunoprecipitated with PA proteins, 351 host proteins were co-immunoprecipitated with HA proteins, 574 host proteins were co-immunoprecipitated with NP proteins, 675 host proteins were co-immunoprecipitated with NA proteins, 659 host proteins were co-immunoprecipitated with M1 proteins, 531 host proteins were co-immunoprecipitated with M2 proteins, 113 host proteins were co-immunoprecipitated with NS1 proteins, 42 host proteins were co-immunoprecipitated with NS2 proteins, and 81 host proteins were co-immunoprecipitated with PB1-F2 proteins. That is, a total of 1292 host proteins were co-immunoprecipitated with any of 11 types of influenza virus proteins.

<siRNA>

Next, RNA interference was performed on genes that encoded the 1292 host proteins identified by immunoprecipitation and it was examined whether these proteins were actually involved in influenza virus propagation. 2 types of siRNA were selected from genome-wide Human siRNA Libraries (FlexiTube siRNA; commercially available from Qiagen) for host genes and used. In addition, AllStars Negative Control siRNA (commercially available from Qiagen) (a control siRNA) was used as a negative control. In addition, siRNA (GGA UCU UAU UUC UUC GGA GUU) of NP genes of WSN virus was purchased from Sigma Aldrich.

Specifically, first, an RNAiMAX Reagent (commercially available from Invitrogen) was used to transfect 2 types of siRNA into HEK293 cells at 25 nM (final concentration: 50 nM) twice.

<Cell Viability>

Viability of cells 24 hours after the second transfection of siRNA was determined according to the appended instructions of CellTiter-Glo assay system (commercially available from Promega Corporation). the ratio of the number of living cells among cells into which each siRNA was introduced to the number of living cells among cells into which the control siRNA was introduced was calculated as cell viability (%).

<qRT-PCR>

Quantitative reverse transcription-PCR (qRT-PCR) was performed on cells before transfection of siRNA and cells 48 hours after transfection and it was confirmed whether expression of target host genes was suppressed due to siRNA.

Specifically, first, in the same manner as in the above <siRNA>, siRNA was transfected into HEK293 cells and cells 48 hours after the second transfection were lysed in the cell lysis buffer to prepare a lysate. Total RNA was extracted from the prepared lysate using the Maxwell 16 LEV simply RNA Tissue Kit (commercially available from Promega Corporation). A reverse transcription reaction was performed using ReverTra Ace qPCR RT Master Mix (commercially available from Toyobo Co., Ltd.) or SuperScript III Reverse Transcriptase (commercially available from Invitrogen) using the total RNA as a template. Using the synthesized cDNA as a template, a primer set specific to each host gene and THUNDERBIRD SYBR qPCR Mix (commercially available from Toyobo Co., Ltd.) were used to perform quantitative PCR. The relative mRNA expression levels of each host gene were calculated by the ΔΔCt method using β-actin as internal control. The ratio of an mRNA expression level in cells into which each siRNA was introduced to an mRNA expression level in cells into which the control siRNA was introduced was calculated as a knockdown efficiency (%).

<Replicative Competence of Virus>

In the same manner as in <siRNA>, in two 24-well dishes, siRNA was transfected into HEK293 cells, and the cells after the second transfection were infected with an influenza virus of 50 pfu (plaque-forming units). A culture supernatant was collected 48 hours after the viral infection and virus titers were examined through a plaque assay using MDCK cells. A value obtained by dividing a common logarithmic value of a virus titer in cells into which each siRNA was introduced by a common logarithmic value of a virus titer in cells into which the control siRNA was introduced was calculated as an amount of change in virus titer.

As a result, in 323 host genes, gene expression levels were reduced due to transfection of siRNA. Among the 323 host genes, in 25 host genes, cell viability was 60% or more, and cell proliferation was not impaired much, but an influenza virus titer increased by a common logarithmic value of 1 or more (that is, an amount of change in the virus titer was 1 or more). The amount of change in virus titer and the cell viability (%) of the 25 host genes are shown in Table 1. Based on such results, it was clarified that cultured cells in which expression of at least one gene among the 25 genes was suppressed had a sufficient proliferative ability, had a high ability to propagate influenza virus, and were suitable for influenza virus production.

TABLE 1

| Gene name | Gene ID | Amount of change in virus titer | Cell viability (%) |
|---|---|---|---|
| ACTG1 | 71 | 1.08 | 90.08 |
| ACTN1 | 87 | 1.75 | 62.89 |
| ATCAY | 85300 | 1.10 | 73.68 |
| CCT6A | 908 | 1.32 | 73.91 |
| COPS7B | 64708 | 1.12 | 95.66 |
| DAP3 | 7818 | 1.11 | 71.45 |
| ERLIN2 | 11160 | 1.35 | 70.12 |
| GNAI2 | 2771 | 1.10 | 71.49 |
| GTF3C5 | 9328 | 1.25 | 111.45 |
| HNRPAB | 3182 | 1.27 | 106.80 |
| KHSRP | 8570 | 1.14 | 82.57 |
| KRT18 | 3875 | 1.06 | 92.54 |
| MTCH1 | 23787 | 1.04 | 98.39 |
| PPP2R1A | 5518 | 1.26 | 71.93 |
| PRPS1 | 5631 | 1.33 | 81.04 |
| RAB18 | 22931 | 1.10 | 86.94 |
| RAB3A | 5864 | 1.30 | 89.61 |
| RAP1B | 5908 | 1.03 | 75.17 |

TABLE 1-continued

| Gene name | Gene ID | Amount of change in virus titer | Cell viability (%) |
|---|---|---|---|
| RPS19 | 6223 | 1.05 | 106.11 |
| RPS7 | 6201 | 1.09 | 60.07 |
| S100A10 | 6281 | 1.16 | 73.57 |
| SFRS7 | 6432 | 1.20 | 109.82 |
| SLC2A12 | 154091 | 1.02 | 110.18 |
| TMED2 | 10959 | 1.02 | 110.74 |
| USP10 | 9100 | 1.00 | 92.80 |

Example 2

In cultured cell line Vero cells derived from kidney epithelial cells of the vervet monkey (*Cercopithecus aethiops*), expression levels of 25 genes described in Table 1 were reduced and an influence on an ability to propagate influenza virus was examined.

The reducing of the expression levels of the genes was performed in the same manner as in Example 1 using siRNA that was used in Example 1 except that Vero cells were used in place of HEK293 cells. Specifically, in the same manner as in <siRNA> of Example 1, siRNA was transfected into Vero cells and cells after the second transfection were infected with an influenza virus of 50 pfu. A culture supernatant was collected 48 hours after the viral infection and virus titers were examined through a plaque assay using MDCK cells. A value obtained by dividing a virus titer (pfu) of cells into which each siRNA was introduced by a virus titer (pfu) of cells into which the control siRNA was introduced was calculated as a virus titer (a relative value (%) to a control). The calculation results are shown in the FIGURE.

As a result, among the 25 types of genes, in 13 types of genes including ACTG1 gene, ACTN1 gene, DAP3 gene, GNAI2 gene, GTF3C5 gene, KRT18 gene, MTCH1 gene, PRPS1 gene, RPS19 gene, S100A10 gene, SFRS7 gene, SLC2A12 gene, and USP10 genes, in cells in which at least one of two types of siRNAs was introduced, the virus titer was higher than in cells into which the control siRNA was introduced. As a result, it was clarified that, when expression of the 13 types of genes is suppressed, an influenza virus propagation promoting effect could be obtained in monkey-derived cultured cells similarly to human-derived cultured cells.

Also, among the 25 types of genes, in the remaining 12 types of genes, no influenza virus propagation promoting effect due to introduction of siRNA was confirmed and the reason for this is speculated to be related to the fact that, since siRNA prepared based on a human genome was used, RNA interference was insufficient and suppression of expression of the genes was not successfully performed.

Example 3

In cultured cell line MDCK cells derived from canine kidney tubular epithelial cells, expression levels of the 25 genes described in Table 1 were reduced and an influence on an ability to propagate influenza virus was examined.

Specifically, an influenza virus was infected into siRNA transfected cells and culture was performed in the same manner as in Example 1 except that MDCK cells were used in place of Vero cells and 3 types of siRNAs rather than two types were selected from genome-wide Human siRNA Libraries and used for host genes. An amount of change in virus titer (a value obtained by dividing a common logarithmic value of a virus titer in cells into which each siRNA was introduced by a common logarithmic value of a virus titer in cells into which the control siRNA was introduced) of a culture supernatant was examined. The measurement results are shown in Table 2.

TABLE 2

| Gene name | Gene ID | Amount of change in virus titer |
|---|---|---|
| USP10 | 479625 | 0.7114 |
| KRT18 | 477601 | 1.0675 |
| PPP2R1A | 484335 | 0.7132 |
| TMED2 | 100687986 | 0.5397 |

As a result, in 4 types of genes including USP10 gene, KRT18 gene, PPP2R1A gene, and TMED2 gene, in cells in which at least one type of siRNA among 3 types of siRNAs was introduced, the amount of change in virus titer was 0.5 or more and the virus titer was higher than in cells into which the control siRNA was introduced. As a result, it was clarified that, when expression of the 4 types of genes was suppressed, an influenza virus propagation promoting effect could be obtained in canine-derived cultured cells similarly to human-derived cultured cells.

Also, among the 25 types of gene, in genes other than the 4 types of genes, no influenza virus propagation promoting effect due to introduction of siRNA was confirmed and the reason for this is speculated to be related to the fact that, since siRNA prepared based on a human genome was used, RNA interference was insufficient and suppression of expression of the genes was not successfully performed.

Example 4

According to RGEN, among 25 types of genes described in Table 1 in MDCK cells, gene-disrupted cells of KRT18 gene and USP10 gene were prepared and productivity of an influenza virus was examined.

Specifically, first, for genes, a guide RNA that recognized a target sequence to be cut in the chromosomes was designed based on base sequence information. Two guide RNAs were designed for one target gene. Next, both an expression vector for expressing a guide RNA in a cell and an expression vector for expressing Cas9 endonuclease in a cell were introduced into MDCK cells and selection was then performed using a drug. From surviving clones according to drug selection, 0 to 20 clones for each cell in which one guide RNA was introduced were picked up as gene-disrupted cells of target genes and individually cultured. The created gene disrupted MDCK cells of the genes were cultured in a minimum essential medium (MEM) under a 5% carbon dioxide atmosphere at 37° C. in a carbon dioxide incubator.

In order to examine influenza virus propagation efficiency of the created gene disrupted MDCK cells, each clone was seeded in three wells in a 12-well plate and cultured in a carbon dioxide incubator at 37° C. for several days. The seeding of each clone in three wells was for triplicate experiments. Confluent cells were confirmed for each well and then washed with MEM. Then, the cells were infected with 0.1 mL of an influenza virus to a multiplicity of infection (MOI; the number of virus infections per cell) of about 0.001 and cultured in a carbon dioxide incubator at 37° C. for 1 hour. After the culture, virus solutions were removed from the wells, MEM containing 1 μg/mL trypsin was added at 1 mL/well, and culture was additionally performed in a carbon dioxide incubator at 37° C. for 2 days. Culture supernatants of the wells after the culture were collected, a plaque assay was performed on the MDCK cells and a virus titer (pfu) was measured. A value obtained by dividing a virus titer (pfu) in the gene disrupted MDCK cells by a virus titer (pfu) in control cells (MDCK cells into which an expression vector containing no guide RNA was introduced in RGEN) was calculated as a virus titer (a relative value (%) to a control). The calculation results are shown in Table 3. The virus titer (a relative value (%) to a control) of each clone in Table 3 shows an average value and an sd of results of 3 wells.

TABLE 3

| | | Virus titer (a relative value (%) to a control) | |
|---|---|---|---|
| Disrupted genes | Clone name | average value | sd |
| KRT18 | 14-2 | 305.30 | 156.25 |
| KRT18 | 14-7 | 191.67 | 54.65 |
| KRT18 | 14-8 | 425.72 | 99.61 |
| KRT18 | 14-9 | 463.88 | 161.93 |
| KRT18 | 14-12 | 363.68 | 50.13 |
| KRT18 | 15-1 | 445.39 | 82.05 |
| KRT18 | 15-4 | 1121.59 | 991.89 |
| KRT18 | 15-6 | 664.14 | 224.78 |
| KRT18 | 15-8 | 646.34 | 247.63 |
| KRT18 | 15-10 | 217.68 | 122.30 |
| KRT18 | 15-11 | 160.86 | 64.84 |
| KRT18 | 15-13 | 561.24 | 454.45 |
| KRT18 | 15-14 | 182.83 | 212.97 |
| KRT18 | 15-15 | 399.45 | 127.89 |
| KRT18 | 15-16 | 190.28 | 93.34 |
| KRT18 | 15-17 | 355.54 | 180.47 |
| USP10 | 36-2 | 170.83 | 87.30 |
| USP10 | 36-3 | 251.64 | 80.40 |
| USP10 | 36-4 | 184.50 | 64.94 |
| USP10 | 36-5 | 232.43 | 142.61 |
| USP10 | 36-7 | 288.51 | 159.33 |
| USP10 | 36-11 | 283.33 | 144.34 |
| USP10 | 36-15 | 208.33 | 62.92 |
| USP10 | 36-17 | 215.77 | 58.35 |
| USP10 | 37-1 | 246.34 | 191.66 |
| USP10 | 37-3 | 189.60 | 26.54 |
| USP10 | 37-5 | 180.91 | 78.93 |
| USP10 | 37-6 | 176.82 | 112.02 |
| USP10 | 37-8 | 213.98 | 70.83 |
| USP10 | 37-9 | 359.47 | 214.63 |
| USP10 | 37-10 | 226.56 | 93.83 |
| USP10 | 37-11 | 204.88 | 91.05 |
| USP10 | 37-12 | 180.04 | 22.97 |
| USP10 | 37-13 | 180.76 | 76.49 |
| USP10 | 37-15 | 188.96 | 95.77 |
| USP10 | 37-17 | 150.37 | 104.91 |

As shown in Table 3, gene-disrupted cells of KRT18 gene and USP10 gene show higher virus titers than control cells and some clones show a virus titer more than three times that of the control cells. The results indicate that productivity of an influenza virus increased in cultured cells in which the function of KRT18 gene or USP10 gene was disrupted.

[Sequence Listing]

The invention claimed is:

1. Cells for producing an influenza virus which are Vero cells or MDCK cells in which expression of TMED2 gene is suppressed and which are able to be cultured in vitro, wherein the cells are infected with influenza virus.

2. Cells for producing an influenza virus which are HEK293 cells in which expression of TMED2 gene is suppressed and which are able to be cultured in vitro, wherein the cells are infected with influenza virus.

3. The cells according to claim 1, wherein the cells in which expression of TMED2 gene is suppressed to 50% or less as compared with cells of the same type before expression suppression.

4. The cells according to claim 2, wherein the cells in which expression of TMED2 gene is suppressed to 50% or less as compared with HEK293 cells before expression suppression.

* * * * *

SEQUENCE LISTING

```
<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: NP gene of
      WSN virus
<400> SEQUENCE: 1
ggaucuuauu ucuucggagu u                                              21
```